United States Patent [19]
Tanaka et al.

[11] Patent Number: 5,773,397
[45] Date of Patent: Jun. 30, 1998

[54] BUBBLE BATH COMPOSITION

[75] Inventors: Norihiro Tanaka; Narushi Takahashi; Junko Suzuki; Hidenori Yorozu, all of Ichikai-machi, Japan

[73] Assignee: Kao Corporation, Tokyo, Japan

[21] Appl. No.: 652,122

[22] Filed: May 23, 1996

[30]     Foreign Application Priority Data

May 23, 1995 [JP] Japan ................................... 6-123758
Jun. 8, 1995 [JP] Japan ................................... 6-141440
Jul. 11, 1995 [JP] Japan ................................... 6-174567

[51] Int. Cl.$^6$ ....................................................... A61K 7/50
[52] U.S. Cl. ........................ 510/119; 510/123; 510/125; 510/126; 510/127; 510/130; 510/135
[58] Field of Search ................... 510/125, 126, 510/127, 130, 135, 119, 123

[56]         References Cited

U.S. PATENT DOCUMENTS 5,039,513  8/1991  Chatterjee et al. ....................... 424/47
5,534,265  7/1996  Fowler et al. ........................... 424/489
5,653,970  8/1997  Vermeer ................................ 424/70.24

OTHER PUBLICATIONS

Garcia Dominguez et al., Chem. Abstract 106:89971, 1987.

*Primary Examiner*—Mukund J. Shah
*Assistant Examiner*—Deepak R. Rao
*Attorney, Agent, or Firm*—Oblon, Spivak, McClelland, Maier & Neustadt, P.C.

[57]         ABSTRACT

The present invention provides a bubble bath composition containing (A) 10–30% by weight of a $C_{8-18}$ alkylalkanolamide surfactant or a $C_{8-18}$ alkyldimethylamino acetic acid betaine surfactant, (B) 5–20% by weight of an anionic surfactant, $C_{8-18}$ alkyl (or polyether-type) sulfate, and (C) 20–80% by weight of a polyol, wherein the ratio by weight of component (A) to component (B) is greater than or equal to 1 and the composition has a viscosity of less than or equal to 1000 cp at 20° C. This composition provides excellent foam producing ability and foam persistence, is readily dispersed in bath water, and imparts moistness to the skin after bathing. The composition of the invention is relaxation due to its rich foam and moisturizing sensation of the skin.

17 Claims, No Drawings

BUBBLE BATH COMPOSITION

BACKGROUND OF THE INVENTION

1. Field of the Invention

The present invention relates to a bubble-producing composition for bath water (hereinafter referred to as a bubble bath composition), and more particularly to a bubble bath composition which produces rich and persistent foam, which is readily dispersed in bath water, and which provides moistness to the skin after bathing.

2. Description of the Background

Bubble bath compositions are known and are typically formulated from body detergents such as anionic surfactants, nonionic surfactants, or amphoteric surfactants (all of which serve as body detergents), oils and fats, and water-soluble humectants.

Bathing in a "bubble bath" is suppose to relax and clean a bather. However, if the water pressure of tap used with the bubble bath composition is not sufficiently high, only small amounts of bubbles are produced. Moreover, even when bubbles are produced, they tend to defoam during bathing. In addition, because the major components of bubble bath compositions are detergents, natural moisturizing components present in the skin are lost during bathing, causing a dry sensation of the skin after bathing. For these and other reasons, use of bubble bath compositions has not yet become popular.

The amount of bubbles or foam produced by a bubble bath composition can be increased by increasing the amounts of surfactants and foam-increasing agents. However, the presence of significant amounts of surfactants further enhances the dry sensation of the skin after bathing. Alternatively, addition of more surfactant results in poor dispersibility of the composition in bath water.

A novel bubble bath composition which produces rich and persistent foam, which is readily dispersed in bath water, and which provides moistness to the skin after bathing is desired.

SUMMARY OF THE INVENTION

Accordingly, one object of the present invention is to provide a bubble bath composition which produces rich and persistent foam, which is readily dispersed in bath water, and which never causes a dry sensation of the skin after bathing.

The present inventors achieved this and other objects with a bubble bath composition comprising:

(A) 10–30% by weight, based on the total weight of the composition, of
  at least one alkylalkanolamide surfactant of the formula (1),

at least one betaine surfactant of the formula (2):

or mixtures thereof:
  wherein $R^1$ is a $C_{7-17}$ alkyl group, $R^2$ is a $C_{8-18}$ alkyl group, and X is a hydrogen atom or a hydroxyethyl group;
(B) 5–20% by weight, based on the total weight of the composition, of an anionic surfactant of the formula (3):

wherein $R^3$ is a $C_{8-18}$ alkyl group, $M^1$ is an anionic residue, and n is an integer from 0 to 10; and
(C) 20–80% by weight, based on the total weight of the composition, of a polyol;
  wherein the ratio by weight of component (A) to component (B) (A/B) is greater than or equal to 1 and wherein the composition has a viscosity of less than or equal to 1000 cp at 20° C.

A second embodiment of the present invention is a bubble bath composition comprising, in addition to the above mentioned components, one or more components selected from the group consisting:
(D) 5–20% by weight, based on the total weight of the composition, of a nonionic surfactant having an HLB value of greater than or equal to 13;
(E) 0.02–1% by weight, based on the total weight of the composition, of a horny layer intercellular lipid or a structural analog thereof;
(F) 0.5–10% by weight, based on the total weight of the composition, of a polyglycerol fatty acid ester having an HLB value of less than or equal to 10; and
(G) 0.1–10% by weight, based on the total weight of the composition, of an extract of a plant belonging to the Gramineae family, the Rutaceae family, or the Araceae family.

DETAILED DESCRIPTION OF PREFERRED EMBODIMENTS

Component (A) can contain one or more alkylalkanolamide surfactant(s) of formula (1), one or more betaine surfactant(s) of formula (2), or mixtures of (1) and (2).

In formula (1), the $C_{7-17}$ alkyl group represented by $R^1$ may be any one of linear alkyl, branched alkyl, cyclic alkyl, or partially cyclic alkyl. $R^1$ is preferably a $C_{12-16}$ linear or branched alkyl. Specific examples of alkylalkanolamide surfactants of formula (1) include, but are not limited to, coconut oil fatty acid diethanolamide, lauric acid diethanolamide, coconut oil fatty acid monoethanolamide, and myristic acid diethanolamide.

In formula (2), the $C_{8-18}$ alkyl group represented by $R^2$ may be any one of linear alkyl, branched alkyl, cyclic alkyl, or partially cyclic alkyl. $R^2$ is preferably a $C_{12-16}$ linear or branched alkyl. Specific examples of betaine surfactants include, but are not limited to, lauryldimethylamino acetic acid betaine and myristyldimethylamino acetic acid betaine.

The amount of component (A) is 10–30% by weight, and preferably 15–25% by weight. Amounts less than 10% by weight result in insufficient persistence of foam, whereas amounts greater than 30% by weight increase the viscosity of the composition, thereby reducing dispersibility of the composition in bath water.

Component (B) can contain one or more anionic surfactant(s) of formula (3). In formula (3), the $C_{8-18}$ alkyl group represented by $R^3$ may be any one of linear alkyl, branched alkyl, cyclic alkyl, or partially cyclic alkyl. $R^3$ is preferably a $C_{12-16}$ linear or branched alkyl. Examples of the anionic residue represented by $M^1$ include alkali metals such as sodium and potassium; mono-, di-, or trialkanolamines such as ethanolamine, diethanolamine, and triethanolamine; and ammonium. The integer n is 0–10, and preferably 0–4. Specific examples of anionic surfactants include, but are not limited to, sodium polyoxyethylene (2–4) laurylether sulfate, polyoxyethylene (2–4) laurylether sulfate triethanolamine, ammonium polyoxyethylene (2–4) laurylether sulfate, laurylsulfate triethanolamine, and sodium laurylsulfate.

The amount of component (B) is 5–20% by weight, and preferably 7–15% by weight. Amounts less than 5% by weight result in insufficient foam producing ability, whereas amounts greater than 20% by weight invite dryness of the skin after bathing, causing an unfavorable texture of the skin.

It is necessary that the ratio by weight of component (A) to component (B) (A/B) be greater than or equal to 1. The ratio is preferably 1.5–3 to 1. If the ratio A/B is less than 1, persistence of foam is significantly reduced, and thus, the effect of the present invention cannot be obtained.

Component (C) is a polyol including dihydric or trihydric alcohols. Specifically, examples of suitable polyols include, but are not limited to, glycerol, 1,3-butylene glycol, propylene glycols, and polyethylene glycols (particularly, those having a molecular weight of 400–20,000).

The amount of component (C) is 20–80% by weight, and preferably 22–40% by weight. Amounts less than 20% by weight results in reduced dispersibility of the composition in bath water, whereas amounts greater than 80% by weight cause insufficient foam-producing ability as the amounts of components (A) and (B) decrease.

The bubble bath compositions of the present invention have a viscosity of not more than 1,000 cp at 20° C., and preferably not more than 500 cp. If the viscosity of a bubble bath composition is in excess of 1,000 cp, the composition cannot easily be taken out of its container. In addition, dispersibility in bath water is reduced. The viscosity values in this specification are measured using a B-type viscometer.

Optional component (D) contains at least one nonionic surfactant having an HLB value of greater than or equal to 13, preferably 13 to 25, for the purpose of improving the texture of the skin after bathing.

Examples of suitable nonionic surfactants include polyoxyethylene alkyl ethers having HLB values of greater than or equal to 13, polyoxyethylene alkenyl ethers having HLB values of greater than or equal to 13, polyoxyethylene sorbitan fatty acid esters having HLB values of greater than or equal to 13, and polyoxyethylene fatty acid esters having HLB values of greater than or equal to 13. Preferably, the alkyl groups of these nonionic surfactants have 10–16 carbon atoms, the alkenyl groups have 16–20 (particularly 18) carbon atoms, and the fatty acid residues have 10–16 carbon atoms. Specific examples of preferred nonionic surfactants include, but are not limited to, polyoxyethylene lauryl ethers (E.O.; the number of added mols=9–50), polyoxyethylene cetyl ethers (E.O.; 10–40), polyoxyethylene oleyl ethers (E.O.; 10–50), polyoxyethylene sorbitan monolaurates (E.O.; 6–20), and polyoxyethylene sorbitan monopalmitates (E.O.; 10–20).

These nonionic surfactants may be used singly or in combinations of 2 or more. In order to maximize the effect of improving the texture of the skin during and after bathing, they are preferably used in amounts of 5–20% by weight, and more preferably 7–15% by weight.

When a horny layer intercellular lipids or a structural analog thereof (E) is incorporated in the bubble bath composition of the present invention, remarkably excellent moistness can be imparted to the skin after bathing. Examples of suitable horny layer intercellular lipids include ceramides, glycosyl ceramides, cholesterols, long-chain fatty acids, and cholesteryl esters. The cholesteryl esters may be those of $C_{8-20}$ saturated or unsaturated, linear or branched fatty acids. The analog may be a ceramide analog, i.e., a lipid derivative constituted by a molecular structure having two long-chain hydrocarbon groups and, between these groups, an OH-group and an amide group, and being capable of taking a planar conformation.

Examples of such compounds include those of the formula (4):

wherein $R^4$ is a $C_{10-26}$ linear or branched, saturated or unsaturated hydrocarbon group and $R^5$ is a $C_{9-25}$ linear or branched, saturated or unsaturated hydrocarbon group. In formula (4), $R^4$ and $R^5$ are preferably linear or branched alkyl or alkenyl groups.

The horny layer intercellular lipids and their structural analogs are incorporated singly or in combinations of two or more. For obtaining moistness of the skin after bathing and foam producing ability simultaneously, they are preferably incorporated in amounts of 0.01–25 by weight.

When a polyglycerol fatty acid ester having an HLB value of 10 or less (F) is incorporated in the bubble bath composition of the present invention, it is possible to improve smoothness of the skin during bathing.

The polyglycerol fatty acid esters having 10 or less HLB values (F) are preferably those in which 4–20 mols, particularly 5–11 mols, of glycerol have been added, and the fatty acid moiety has 8–20 carbon atoms, and particularly 16–18 carbon atoms. Specific examples include, but are not limited to, decaoleic acid decaglycerols, decaglycerol pentaoleic acid esters, monooleic acid diglycerols, stearic acid decaglycerols, and decastearic acid decaglycerols. The component (F) is preferably incorporated in amounts of 0.5–10% by weight. If the amounts are less than 0.1% by weight, feel to the touch of the skin is not improved and sebum-resistant foam production is not expected. On the other hand, amounts greater than 10% by weight can no longer exhibit significant improvement.

When the bubble bath composition of the present invention contains an extract of a plant belonging to the Gramineae family, the Rutaceae family, or the Araceae family, itchiness of the skin occurrable after bathing can be suppressed.

Examples of plants belonging to the Gramineae family include, but are not limited to, oats and adlay; plants belonging to the Rutaceae family include, but are not limited to, *Citrus unshu*, *Citrus aurantium*, and citron; and plants belonging to the Araceae family include, but are not limited to, the Japanese iris and sekisho. These extracts may be used singly or in combinations of two or more. Extraction may be performed through routine methods such as extraction with hot water, extraction with ethanol, and extraction with 1,3-butylene glycol.

The extracts preferably contain 2–30 w/v% of evaporation residues. They are preferably incorporated in amounts of 0.1–10% by weight, particularly 0.2–5% by weight, in the composition of the present invention. If the amounts are less than 0.1% by weight, itchiness occurrable after bathing cannot be suppressed, whereas amounts greater than 10% by weight result in a poor foam producing ability.

Each of components (D), (E), (F), and (G) may be incorporated in the bubble bath composition of the present invention singly or in combinations of two or more.

The bubble bath composition of the present invention may contain, in addition to the above-mentioned components, preservatives, perfumes, colorants, water, vitamins, inorganic salts, amino acids, etc.

The bubble bath composition according to the present invention may contain a cool-feeling agent to give a bather refreshing-feeling after bathing. Preferable cool-feeling agents include, but are not limited to, 1-menthol, camphor, 1-menthone, 1-spearmint, 1-peppermint, borneol, and cineol. Of these, 1-menthol is more preferable. The cool-feeling agent can be used singly or in combinations. The amount thereof ranges from 0.1 to 10% by weight. Incorporating the cool-feeling agent less than −0.1% by weight causes little effect of refreshing-feeling, while incorporating the agents more than 10% by weight causes excessive cool-feeling such that feeling in use is deteriorated. The amount of the cool-feeling agent ranges preferably from 0.3 to 8% by weight, and more preferably from 0.6 to 5% by weight.

The bubble bath composition of the present invention may be prepared by mixing the above-described components. The resulting composition is usually a liquid or an emulsion.

The bubble bath composition of the present invention may be used in a manner such that a suitable amount of the bubble bath composition is added to bath water (for example, 10–30 ml per 150 liters of bath water), and then tap water or hot water is added to produce bubbles, or tap water or hot water is showered onto the surface of the bath water to produce bubbles, or the bath water is stirred to produce bubbles.

Having generally described this invention, a further understanding can be obtained by reference to certain specific examples which are provided herein for purposes of illustration only and are not intended to be limiting unless otherwise specified.

EXAMPLES

Example 1

Liquid bubble bath compositions shown in Tables 1 through 4 were prepared using a routine method and assessed in terms of foam producing ability, foam persistence, dispersibility in bath water, and moistness of the skin after bathing.

(1) Method for testing foam producing ability:

Each sample (10 ml) which had been prepared to have a concentration of 0.02% using 40 DH hard water was placed in a 100-ml color comparison tube (φ 24 mm), and heated to 40° C. When the temperature of the sample reached 40° C., it was vigorously shaken vertically 15 times (time/sec) and the height of foam produced after 30 seconds was measured.

(2) Method for testing foam persistence and moistness of the skin after bathing:

Each bubble bath composition (20 ml) was placed in a bathtub, and warm water (39° C., 150 liters) was added to the bathtub so that bubbles were formed. Each panelist took a bath, immersing up to the neck, and made assessment based on the following evaluation standards The results of assessment are shown as average ratings of 10 panelists.

Persistence of foam

The state of foam after 20 minutes of bathing was evaluated based on the following standards:

5: No reduction of foam

4: Almost no reduction of foam

3: Slight reduction of foam

2: Considerable reduction of foam

1: Disappearance of foam

Moistness of the skin after bathing

The state of the skin 30 minutes after getting out of the bath was evaluated based on the following standards:

5: Moistened sensation

4: Slightly moistened sensation

3: Comparable to bath water containing no additives

2: Slightly dry sensation

1: Dry sensation (3) Test method for dispersibility in bath water:

The state observed in the case where each bubble bath composition was added to warm bath water (40° C.) was compared with the case where the composition was added to colored water (water containing only a dye).

Evaluation was made based on the following standards:

5: Readily dispersed

4: Moderately dispersed

3: Comparable to the case of colored water

2: Slightly difficult to be dispersed

1: Difficult to be dispersed

The results are shown in Tables 1 through 4. As can be understood from the Tables, results were satisfactory with respect to all the evaluation items, i.e., foam producing ability, foam persistence, dispersibility in bath water, and moistness of the skin after bathing, only when the amounts of respective components, ratio of components, etc. were within the ranges defined by the present invention.

TABLE 1

| | (% by weight) Compositions | | | | | | |
| --- | --- | --- | --- | --- | --- | --- | --- |
| | 1 | 2 | 3 | 4 | 5 | 6 | 7 |
| Lauric acid diethanolamide | 20 | 20 | 20 | 20 | 20 | — | 10 |
| Sodium POE(3) laurylether sulfate | 10 | 10 | 10 | 10 | — | 10 | 20 |
| POE(23) Lauryl ether | — | 10 | — | — | — | — | — |
| Cholesteryl isostearate | — | — | 0.05 | — | — | — | — |
| Propylene glycol | 30 | 30 | 30 | 10 | 30 | 30 | 30 |
| Glycerol | — | — | — | 15 | — | — | — |
| Methyl p-oxybenzoate | 0.2 | 0.2 | 0.2 | 0.2 | 0.2 | 0.2 | 0.2 |
| Butyl p-oxybenzoate | 0.2 | 0.2 | 0.2 | 0.2 | 0.2 | 0.2 | 0.2 |
| Perfume | 1.0 | 1.0 | 1.0 | 1.0 | 1.0 | 1.0 | 1.0 |
| Colorant | | | trace amount | | | | |
| Ion exchange water | | | balance | | | | |
| Component (A)/Component (B) | 2 | 2 | 2 | 2 | ∞ | 0 | 0.5 |
| Viscosity (20° C.) cp | 41 | 77 | 40 | 200 | 20 | 8 | 56 |
| Height of foam (MM) | 16 | 17 | 16 | 18 | 1 | 10 | 19 |

TABLE 1-continued

| | (% by weight) Compositions | | | | | | |
|---|---|---|---|---|---|---|---|
| | 1 | 2 | 3 | 4 | 5 | 6 | 7 |
| Persistence of foam | 4.1 | 4.2 | 4.0 | 4.0 | 1.2 | 1.8 | 2.8 |
| Dispersibility in bath water | 4.5 | 4.3 | 4.2 | 4.2 | 4.4 | 4.6 | 4.5 |
| Moistness after bathing | 3.2 | 3.9 | 4.7 | 3.2 | 2.7 | 1.7 | 1.5 |

TABLE 2

| | (% by weight) Compositions | | |
|---|---|---|---|
| | 8 | 9 | 10 |
| Lauric acid diethanolamide | 50 | 20 | 50 |
| Sodium POE(3) laurylether sulfate | 10 | 10 | 10 |
| POE(23) Lauryl ether | — | — | — |
| Cholesteryl isostearate | — | — | — |
| Propylene glycol | 30 | 10 | 10 |
| Methyl p-oxybenzoate | 0.2 | 0.2 | 0.2 |
| Butyl p-oxybenzoate | 0.2 | 0.2 | 0.2 |
| Perfume | 1.0 | 1.0 | 1.0 |
| Colorant | | trace amount | |
| Ion exchange water | | balance | |
| Component (A)/Component (B) | 5 | 2 | 5 |
| Viscosity (20° C.) cp | 139 | 153 | 1440 |
| Height of foam (MM) | 18 | 15 | 19 |
| Persistence of foam | 4.0 | 4.1 | 4.1 |
| Dispersibility in bath water | 3.0 | 2.1 | 1.8 |
| Moistness after bathing | 1.4 | 2.8 | 1.2 |

TABLE 3

| | (% by weight) Compositions | | | | | | |
|---|---|---|---|---|---|---|---|
| | 11 | 12 | 13 | 14 | 15 | 16 | 17 |
| Lauryldimethylamino acetic acid betaine | 15 | 15 | 15 | 15 | 15 | — | 8 |
| Sodium POE(3) laurylether sulfate | 10 | 10 | 10 | 10 | — | 10 | 20 |
| POE(23) Lauryl ether | — | 15 | — | — | — | — | — |
| Cholesteryl isostearate | — | — | 0.10 | — | — | — | — |
| Propylene glycol | 40 | 40 | 40 | 10 | 40 | 40 | 40 |
| Glycerol | — | — | — | 15 | — | — | — |
| Methyl p-oxybenzoate | 0.2 | 0.2 | 0.2 | 0.2 | 0.2 | 0.2 | 0.2 |
| Butyl p-oxybenzoate | 0.2 | 0.2 | 0.2 | 0.2 | 0.2 | 0.2 | 0.2 |
| Perfume | 1.0 | 1.0 | 1.0 | 1.0 | 1.0 | 1.0 | 1.0 |
| Colorant | | | | trace amount | | | |
| Ion exchange water | | | | balance | | | |
| Component (A)/Component (B) | 1.5 | 1.5 | 1.5 | 1.5 | ∞ | 0 | 0.4 |
| Viscosity (20° C.) cp | 30 | 62 | 29 | 150 | 13 | 5 | 41 |
| Height of foam (MM) | 15 | 18 | 15 | 16 | 2 | 9 | 18 |
| Persistence of foam | 4.0 | 4.2 | 3.9 | 4.0 | 1.3 | 1.8 | 2.4 |
| Dispersibility in bath water | 4.1 | 4.4 | 4.6 | 4.1 | 4.2 | 4.5 | 4.4 |
| Moistness after bathing | 3.1 | 3.8 | 4.7 | 3.1 | 2.1 | 1.5 | 1.4 |

TABLE 4

| | (% by weight) Compositions | | |
|---|---|---|---|
| | 18 | 19 | 20 |
| Lauryldimethylamino acetic acid betaine | 40 | 15 | 40 |
| Sodium POE(3) laurylether sulfate | 10 | 10 | 10 |
| Cholesteryl isostearate | — | — | — |

TABLE 4-continued

| | (% by weight) Compositions | | |
|---|---|---|---|
| | 18 | 19 | 20 |
| Propylene glycol | 40 | 15 | 5 |
| Methyl p-oxybenzoate | 0.2 | 0.2 | 0.2 |
| Butyl p-oxybenzoate | 0.2 | 0.2 | 0.2 |
| Perfume | 1.0 | 1.0 | 1.0 |
| Colorant | | trace amount | |
| Ion exchange water | | balance | |
| Component (A)/Component (B) | 4 | 1.5 | 4 |
| Viscosity (20° C.) cp | 110 | 120 | 1360 |
| Height of foam (MM) | 17 | 10 | 18 |
| Persistence of foam | 4.0 | 3.4 | 4.1 |
| Dispersibility in bath water | 3.2 | 2.1 | 1.2 |
| Moistness after bathing | 1.2 | 2.8 | 1.1 |

Example 2

Liquid bubble bath compositions shown in Tables 5 and 6 were prepared using a routine method and assessed in terms of foam producing ability, foam persistence, dispersibility in bath water, and smoothness of the skin during bathing.

(1) Method for testing foam producing ability:

A model sebum (1.6 mg) and each sample (10 ml) which had been prepared to have a concentration of 0.02% were both placed in a 100-ml color comparison tube (φ 24 mm), and the tube was heated to 40° C. When the temperature of the contents of the tube reached 40° C., the tube was vigorously shaken 15 times (time/sec) vertically, and the height of foam produced after 30 seconds was measured.

Composition of the model sebum:
Cotton seed oil 50% by weight
Myristyl myristate 25% by weight
Squalane 10% by weight
Cholesterol 5% by weight
Palmitic acid 5% by weight
Oleic acid 5% by weight (2) Method for testing foam persistence and smoothness of the skin during bathing:

In a bathtub containing 1 g of the model sebum, each bubble bath composition (20 ml) was placed. Warm water (39° C., 150 liters) was added to the bathtub so that bubbles were formed. Each panelist took a bath, immersing up to the neck, and made assessment based on the following evaluation standards. The results of assessment are shown as average ratings of 10 panelists.

Persistence of foam

The state of foam after 20 minutes of bathing was evaluated in a manner similar to that employed in Example 1.

Smoothness of the skin during bathing

The state of the skin during bathing was evaluated based on the following standards:

5: Smooth sensation

4: Slightly smooth sensation

3: Comparable to bath water containing no additives

2: Slightly rough sensation

1: Rough sensation (3) Test method for dispersibility in bath water:

Assessment was made in a manner similar to that employed in Example 1.

The results are shown in Tables 5 and 6. As can be understood from the Tables, results were satisfactory with respect to all the evaluation items, i.e., foam producing ability, foam persistence, dispersibility in bath water, and smoothness of the skin after bathing, only when the amounts of respective components, ratio of components, etc. were within the ranges defined by the present invention.

In Tables 5 and 6, compositions 23, 24, 29, and 30, which fall within the scope of the present invention, do not contain component (F). They were evaluated as excellent with respect to all the evaluation items excepting smoothness of the skin during bathing.

TABLE 5

| | (% by weight) Compositions | | | | | | | |
|---|---|---|---|---|---|---|---|---|
| | 21 | 22 | 23 | 24 | 25 | 26 | 27 | 28 |
| Lauric acid diethanolamide | 20 | 20 | 20 | 20 | 10 | 50 | 20 | 50 |
| Sodium POE(3) laurylether sulfate | 10 | 10 | 10 | 10 | 20 | 10 | 10 | 10 |
| Monooleic acid decaglycerol (HLB14.5) | — | — | — | 2.0 | — | — | — | — |
| Decaglycerol pentaoleate (HLB5.0) | 2.0 | 1.0 | — | — | 2.0 | 2.0 | 2.0 | 2.0 |
| Propylene glycol | 30 | 10 | 30 | 30 | 30 | 30 | 10 | 10 |
| Glycerol | — | 15 | — | — | — | — | — | — |
| Methyl p-oxybenzoate | 0.2 | 0.2 | 0.2 | 0.2 | 0.2 | 0.2 | 0.2 | 0.2 |
| Butyl p-oxybenzoate | 0.2 | 0.2 | 0.2 | 0.2 | 0.2 | 0.2 | 0.2 | 0.2 |
| Perfume | 1.0 | 1.0 | 1.0 | 1.0 | 1.0 | 1.0 | 1.0 | 1.0 |
| Colorant | | | | trace amount | | | | |
| Ion exchange water | | | | balance | | | | |
| Component (A)/Component (B) | 2 | 2 | 2 | 2 | 0.5 | 5 | 2 | 5 |
| Viscosity (25° C.) cp | 41 | 202 | 41 | 43 | 58 | 141 | 155 | 1442 |
| Height of foam (MM) | 8 | 9 | 6 | 6 | 9 | 9 | 7 | 9 |
| Persistence of foam | 4.4 | 4.6 | 3.2 | 3.4 | 2.1 | 4.0 | 3.8 | 4.1 |
| Dispersibility in bath water | 4.5 | 4.3 | 4.4 | 4.6 | 4.5 | 3.0 | 2.0 | 1.8 |
| Smoothness during bathing | 4.6 | 4.5 | 2.6 | 2.8 | 2.4 | 3.6 | 3.3 | 3.4 |

TABLE 6

| | (% by weight) Compositions | | | | | | | |
|---|---|---|---|---|---|---|---|---|
| | 29 | 30 | 31 | 32 | 33 | 34 | 35 | 36 |
| Lauryldimethylamino acetic acid betaine | 15 | 15 | 15 | 15 | 8 | 40 | 15 | 40 |
| Sodium POE(3) laurylether sulfate | 10 | 10 | 10 | 10 | 20 | 10 | 10 | 10 |
| Monooleic acid decaglycerol (HLB14.5) | — | — | — | 2.0 | — | — | — | — |
| Decaglycerol pentaoleate (HLB5.0) | 2.0 | 1.0 | — | — | 2.0 | 2.0 | 2.0 | 2.0 |
| Propylene glycol | 40 | 10 | 40 | 40 | 40 | 40 | 15 | 5 |
| Glycerol | — | 15 | — | — | — | — | — | — |
| Methyl p-oxybenzoate | 0.2 | 0.2 | 0.2 | 0.2 | 0.2 | 0.2 | 0.2 | 0.2 |
| Butyl p-oxybenzoate | 0.2 | 0.2 | 0.2 | 0.2 | 0.2 | 0.2 | 0.2 | 0.2 |
| Perfume | 1.0 | 1.0 | 1.0 | 1.0 | 1.0 | 1.0 | 1.0 | 1.0 |
| Colorant | | | | trace amount | | | | |
| Ion exchange water | | | | balance | | | | |
| Component (A)/Component (B) | 1.5 | 1.5 | 1.5 | 1.5 | 0.4 | 4 | 1.5 | 4 |

TABLE 6-continued

|  | (% by weight) Compositions | | | | | | | |
|---|---|---|---|---|---|---|---|---|
|  | 29 | 30 | 31 | 32 | 33 | 34 | 35 | 36 |
| Viscosity (25° C.) cp | 32 | 152 | 30 | 32 | 43 | 112 | 122 | 1362 |
| Height of foam (MM) | 7 | 18 | 5 | 5 | 7 | 8 | 6 | 8 |
| Persistence of foam | 4.2 | 4.4 | 3.4 | 3.3 | 3.0 | 4.0 | 3.6 | 4.1 |
| Dispersibility in bath water | 4.1 | 4.4 | 4.2 | 4.5 | 4.4 | 3.2 | 2.6 | 1.3 |
| Smoothness during bathing | 4.7 | 4.6 | 3.0 | 3.2 | 2.4 | 3.4 | 3.0 | 3.3 |

Example 3

Liquid bubble bath compositions shown in Tables 7 and 8 were prepared using a routine method, and assessed in terms of foam producing ability, foam persistence, dispersibility in bath water, and itchiness of the skin after bathing.

(1) Method for testing foam producing ability:

Foam producing ability was assessed in a manner similar to that described in Example 1.

(2) Method for testing foam persistence and itchiness of the skin after bathing:

Each bubble bath composition (20 ml) was placed in a bathtub. Warm water (39° C., 150 liters) was added to the bathtub so that bubbles were formed. Cups each measuring 3 cm in diameter were attached to 2 portions of the forearms of each panelist (a total of 4 cups for one panelist), and the corresponding skin was defatted for 5 minutes using an acetone:ether (1:1) solution. Subsequently, each of the panelists took a bath, immersing up to the neck, and made assessment based on the following evaluation standards. The results of assessment are shown as average ratings of 10 panelists.

Persistence of foam

The state of foam after 20 minutes of bathing was evaluated in a manner similar to that employed in Example 1.

Itchiness of the skin after bathing

Itchiness of the defatted portions of skin after bathing was evaluated based on the following standards:

5: Intolerably itchy (both arms)

4: Intolerably itchy (single arm)

3: Itchy (both arms)

2: Itchy (single arm)

1: No itchy sensation (3) Test method for dispersibility in bath water:

Assessment was made in a manner similar to that employed in Example 1.

The results are also shown in Tables 7 and 8. As can be understood from the Tables, when the amounts of respective components, ratio of components, etc. were within the ranges defined by the present invention, results were satisfactory with respect to all the evaluation items, i.e., foam producing ability, foam persistence, dispersibility in bath water, and itchiness of the skin after bathing.

In Tables 7 and 8, compositions 40 and 47, both falling within the scope of the present invention, do not contain component (G). They were evaluated as excellent with respect to all the evaluation items excepting itchiness of the skin after bathing.

TABLE 7

|  | (% by weight) Compositions | | | | | | |
|---|---|---|---|---|---|---|---|
|  | 37 | 38 | 39 | 40 | 41 | 42 | 43 |
| Lauric acid diethanolamide | 20 | 20 | 20 | 20 | 10 | 50 | 50 |
| Sodium POE(3) laurylether sulfate | 10 | 10 | 10 | 10 | 20 | 10 | 10 |
| Citrus Unshu peel extract (Evaporation residue: 15 w/v %) | 0.4 | — | — | — | — | — | — |
| Japanese iris extract (Evaporation residue: 5 w/v %) | — | 5.0 | — | — | — | — | — |
| Oats extract (Evaporation residue: 3 w/v %) | — | — | 1.0 | — | 1.0 | 1.0 | 1.0 |
| Propylene glycol | 30 | 30 | 30 | 30 | 30 | 30 | 10 |
| Methyl p-oxybenzoate | 0.2 | 0.2 | 0.2 | 0.2 | 0.2 | 0.2 | 0.2 |
| Butyl p-oxybenzoate | 0.2 | 0.2 | 0.2 | 0.2 | 0.2 | 0.2 | 0.2 |
| Perfume | 1.0 | 1.0 | 1.0 | 1.0 | 1.0 | 1.0 | 1.0 |
| Colorant | trace amount | | | | | | |
| Ion exchange water | balance | | | | | | |
| Component (A)/Component (B) | 2 | 2 | 2 | 2 | 0.5 | 5 | 5 |
| Viscosity (25° C.) cp | 41 | 43 | 45 | 41 | 56 | 140 | 1445 |
| Height of foam (MM) | 18 | 19 | 18 | 16 | 18 | 19 | 18 |
| Persistence of foam | 4.1 | 4.3 | 4.0 | 4.1 | 2.9 | 4.0 | 4.1 |
| Dispersibility in bath water | 4.5 | 4.4 | 4.2 | 4.5 | 4.5 | 3.0 | 1.7 |
| Itchiness of the skin after bathing | 1.2 | 1.1 | 1.2 | 2.7 | 4.0 | 3.5 | 3.7 |

TABLE 8

|  | (% by weight) Compositions | | | | | | |
|---|---|---|---|---|---|---|---|
|  | 44 | 45 | 46 | 47 | 48 | 48 | 49 |
| Lauryldimethylamino acetic acid betaine | 15 | 15 | 15 | 15 | 8 | 40 | 40 |
| Sodium POE(3) laurylether sulfate | 10 | 10 | 10 | 10 | 20 | 10 | 10 |
| Citrus Unshu peel extract (Evaporation residue: 15 w/v %) | 0.4 | — | — | — | — | — | — |
| Japanese iris extract (Evaporation residue: 5 w/v %) | — | 5.0 | — | — | — | — | — |
| Oats extract (Evaporation residue: 3 w/v %) | — | — | 1.0 | — | 1.0 | 1.0 | 1.0 |
| Propylene glycol | 40 | 40 | 40 | 40 | 40 | 40 | 5 |
| Methyl p-oxybenzoate | 0.2 | 0.2 | 0.2 | 0.2 | 0.2 | 0.2 | 0.2 |
| Butyl p-oxybenzoate | 0.2 | 0.2 | 0.2 | 0.2 | 0.2 | 0.2 | 0.2 |
| Perfume | 1.0 | 1.0 | 1.0 | 1.0 | 1.0 | 1.0 | 1.0 |
| Colorant | trace amount | | | | | | |
| Ion exchange water | balance | | | | | | |
| Component (A)/Component (B) | 1.5 | 1.5 | 1.5 | 1.5 | 0.4 | 4 | 4 |
| Viscosity (25° C.) cp | 30 | 32 | 35 | 30 | 41 | 110 | 1365 |
| Height of foam (MM) | 16 | 18 | 17 | 15 | 18 | 17 | 18 |
| Persistence of foam | 4.0 | 4.3 | 4.2 | 4.0 | 2.4 | 4.0 | 4.1 |
| Dispersibility in bath water | 4.1 | 4.2 | 4.4 | 4.1 | 4.4 | 3.2 | 1.3 |
| Itchiness of the skin after bathing | 1.2 | 1.2 | 1.1 | 2.9 | 3.8 | 3.3 | 3.7 |

As described above, the bubble bath compositions of the present invention provide excellent foam producing ability and foam persistence, are readily dispersed in bath water, and impart moistness to the skin after bathing. Therefore, the compositions of the invention provide the relaxation effect due to their rich foam as well as the detergent effect without causing a dry sensation of the skin.

Example 4

A liquid bubble bath composition was prepared by a routine method and contained the following ingredients:

| Ingredients | Composition |
|---|---|
| Lauric acid diethanolamide | 20   (% by weight) |
| Sodium POE(3) laurylether sulfate | 10 |
| L-menthol | 0.5 |
| Propylene glycol | 10 |
| Glycerol | 15 |
| Methyl p-oxybenzoate | 0.2 |
| Butyl p-oxybenzoate | 0.2 |
| Perfume | 1.0 |
| Colorant | trace amount |
| Ion exchange water | balance |
| Component (A)/Component (B) | 2 |
| Viscosity (25° C.) cp | 200 |

Evaluation

This bubble bath composition was evaluated as excellent with respect to persistence of foam during bathing, dispersibility in bath water, and refreshing-feeling after bathing.

Obviously, numerous modifications and variations of the present invention are possible in light of the above teachings. It is therefore to be understood that within the scope of the appended claims, the invention may be practiced otherwise than as specifically described herein.

The present specification is based on JP 123758/1995, filed on May 23, 1995, JP 141440/1995 filed on Jun. 8, 1995 and JP 174567/1995 filed on Jul. 11, 1995. The text of these applications are fully incorporated herein by reference.

What is claimed as new and desired to be secured by Letters Patent of the United States is:

1. A composition comprising:

(A) 10–30% by weight, based on the total weight of the composition, of an alkylalkanolamide surfactant of the formula (1) or a betaine surfactant of the formula (2):

wherein $R^{1'}$ is a $C_{7-17}$ alkyl group, $R^2$ is a $C_{8-18}$ alkyl group, and X is a hydrogen atom or a hydroxyethyl group;

(B) 5–20% by weight, based on the total weight of the composition, of an anionic surfactant of the formula (3):

wherein $R^3$ is a $C_{8-18}$ alkyl group, $M^1$ is an anionic residue, and n is an integer from 0 to 10; and (C) 20–80% by weight, based on the total weight of the composition, of a polyol;

wherein the ratio by weight of component (A) to component (B) is greater than or equal to 1 and the composition has a viscosity of less than or equal to 1000 cp at 20° C.

2. The composition of claim 1, wherein component (A) is of the formula (1).

3. The composition of claim 2, wherein component (A) is coconut oil fatty acid diethanolamide, lauric acid diethanolamide, coconut oil fatty acid monoethanolamide, or myristic acid diethanolamide.

4. The composition of claim 1, wherein component (A) is of the formula (2).

5. The composition of claim 4, wherein component (A) is lauryl-dimethylamino acetic acid betaine or myristyldimethylamino acetic acid betaine.

6. The composition of claim 1, wherein component (B) is sodium polyoxyethylene (2–4) laurylether sulfate, polyoxyethylene (2–4) laurylether sulfate triethanolamine, ammonium polyoxyethylene (2–4) laurylether sulfate, laurylsulfate triethanolamine or sodium laurylsulfate.

7. The composition of claim 1, wherein component (C) is a dihydric or trihydric alcohol.

8. The composition of claim 7, wherein component (C) is glycerol, 1,3-butylene glycol, propylene glycols or a polyethylene glycol having a molecular weight of 400–20,000.

9. The composition of claim 1, further comprising at least one component selected from the group consisting of:

(D) 5–20% by weight, based on the total weight of the composition, of a nonionic surfactant having an HLB value of greater than or equal to 13;

(E) 0.02–1% by weight, based on the total weight of the composition, of a horny layer intercellular lipid or a structural analog thereof;

(F) 0.5–10% by weight, based on the total weight of the composition, of a polyglycerol fatty acid ester having an HLB value of less than or equal to 10;

(G) 0.1–10% by weight, based on the total weight of the composition, of an extract of a plant belonging to the Gramineae family, the Rutaceae family, or the Araceae family; and mixtures thereof.

10. The composition of claim 9, wherein component (D) is a polyoxyethylene alkyl ether, polyoxyethylene alkenyl ether, polyoxyethylene sorbitan fatty acid ester, polyoxyethylene fatty acid ester or a mixture thereof.

11. The composition of claim 9, wherein component (E) is a ceramide, sugar ceramide, cholesterol, long-chain fatty acid, cholesteryl ester or a compound of the formula (4):

wherein $R^4$ is a $C_{10-26}$ linear or branched, saturated or unsaturated hydrocarbon group and $R^5$ is a $C_{9-25}$ linear or branched, saturated or unsaturated hydrocarbon group.

12. The composition of claim 9, wherein component (F) is a decaoleic acid decaglycerol, decaglycerol pentaoleic acid ester, monooleic acid diglycerol, stearic acid decaglycerol or decastearic acid decaglycerol.

13. The composition of claim 9, wherein component (G) is an extract of oats, adlay, *Citrus unshu, Citrus aurantium*, citron, Japanese iris or sekisho.

14. The composition of claim 1, which further comprises a preservative, perfume, colorant, water, vitamin, inorganic salt, amino acid or a mixture thereof.

15. The composition of claim 9, which further comprises a preservative, perfume, colorant, water, vitamin, inorganic salt, amino acid or a mixture thereof.

16. A composition comprising:

(A) 10–30% by weight, based on the total weight of the composition, of an alkylalkanolamide surfactant of the formula (1) or a betaine surfactant of the formula (2):

wherein $R^1$ is a $C_{7-17}$ alkyl group, $R^2$ is a $C_{8-18}$ alkyl group, and X is a hydrogen atom or a hydroxyethyl group;

(B) 5–20% by weight, based on the total weight of the composition, of an anionic surfactant of the formula (3):

wherein $R^3$ is a $C_{8-18}$ alkyl group, $M^1$ is an anionic residue, and n is an integer from 0 to 10; and (C) 20–80% by weight, based on the total weight of the composition, of a polyol;

(D) 0.1–10% by weight, based on the total weight of the composition, of a cool-feeling agent;

wherein the ratio by weight of component (A) to component (B) is greater than or equal to 1 and the composition has a viscosity of less than or equal to 1000 cp at 20° C.

17. The composition of claim 1, wherein the weight ratio of the component (A) to component (B) ranges from 1.5–3 to 1.

* * * * *